US010513481B2

United States Patent
Lépine et al.

(10) Patent No.: US 10,513,481 B2
(45) Date of Patent: Dec. 24, 2019

(54) METHOD AND SYSTEM FOR RECYCLING SPENT ETHYLENE GLYCOL FROM RECOVERED AIRCRAFT DE-ICING SOLUTION

(71) Applicant: AÉRO MAG 2000 RRR INC., St-Laurent (CA)

(72) Inventors: Mario Lépine, Dorval (CA); Ghislain Bergeron, Saint-Eustache (CA); Michel Guy, Pierrefonds (CA)

(73) Assignee: AÉRO MAG 2000 RRR INC., St-Laurent (CA)

( * ) Notice: Subject to any disclaimer, the term of this patent is extended or adjusted under 35 U.S.C. 154(b) by 0 days.

(21) Appl. No.: 15/999,771

(22) Filed: Sep. 5, 2018

(65) Prior Publication Data

US 2019/0010105 A1 Jan. 10, 2019

Related U.S. Application Data

(62) Division of application No. 14/999,007, filed on Mar. 17, 2016, now Pat. No. 10,144,688.

(51) Int. Cl.
| | | |
|---|---|---|
| *B01D 3/14* | (2006.01) | |
| *C07C 29/80* | (2006.01) | |
| *C07C 29/76* | (2006.01) | |
| *B01D 3/42* | (2006.01) | |
| *B01D 15/08* | (2006.01) | |
| *B01D 61/14* | (2006.01) | |

(52) U.S. Cl.
CPC .............. *C07C 29/80* (2013.01); *B01D 3/148* (2013.01); *B01D 3/42* (2013.01); *B01D 15/08* (2013.01); *B01D 61/145* (2013.01); *C07C 29/76* (2013.01); *B01D 2311/246* (2013.01); *B01D 2311/2626* (2013.01); *B01D 2311/2649* (2013.01)

(58) Field of Classification Search
CPC ......... C07C 29/76; C07C 29/80; B01D 3/148; B01D 3/42; B01D 15/08; B01D 61/145
See application file for complete search history.

(56) References Cited

U.S. PATENT DOCUMENTS

| | | | | |
|---|---|---|---|---|
| 4,332,643 A | * | 6/1982 | Reid ...................... | B01D 3/143 |
| | | | | 159/DIG. 10 |
| 5,104,068 A | * | 4/1992 | Krilla ..................... | B64F 5/20 |
| | | | | 134/123 |
| 5,171,767 A | * | 12/1992 | Buckley ............... | B01D 61/145 |
| | | | | 523/310 |

(Continued)

*Primary Examiner* — Jonathan Miller
(74) *Attorney, Agent, or Firm* — Guy J. Houle; Houle Patent Agency Inc.

(57) ABSTRACT

A method and a system for recycling spent ethylene or propylene glycol recovered from aircraft deicing solutions is described. The recovered spent ethylene or propylene glycol contains water and other undesirable substances which require to be removed to produce a solution free of these substances which can be further processed to remove substantially all of the water content and to blend-in additives required to certify the final glycol solution for aircraft deicing. The method and system employs a computer controller for continuous automatic batch processing of the spent glycol, including, in combination, filtering, distillation, blending and testing in specific sequences and achieves an improved quality recycled glycol of a purity of at least 99.5% and preferably between 99.6% to 99.9% glycol concentration.

10 Claims, 3 Drawing Sheets

(56) References Cited

U.S. PATENT DOCUMENTS

| | | | | |
|---|---|---|---|---|
| 5,262,013 A * | 11/1993 | Beal | B01D 3/10 202/160 |
| 5,411,668 A * | 5/1995 | Pollmann | C09K 3/185 210/638 |
| 5,500,095 A * | 3/1996 | Shinagawa | B01D 3/322 159/DIG. 19 |
| 5,552,023 A * | 9/1996 | Zhou | B01D 61/025 159/DIG. 27 |
| 5,635,071 A * | 6/1997 | Al-Samadi | B01D 61/022 210/641 |
| 5,904,321 A * | 5/1999 | Cox | B64F 5/20 203/18 |
| 6,187,197 B1 * | 2/2001 | Haddock | B01D 61/022 204/542 |
| 6,236,332 B1 * | 5/2001 | Conkright | G08C 17/02 340/3.1 |
| 6,638,397 B1 * | 10/2003 | Camiener | B01D 3/14 202/161 |
| 6,849,155 B2 * | 2/2005 | Akita | B01D 1/065 159/44 |
| 7,713,319 B2 * | 5/2010 | Radhakrishnan | B01D 17/085 202/163 |
| 10,144,688 B2 * | 12/2018 | Lepine | C07C 29/80 |
| 2003/0127154 A1 * | 7/2003 | Kneringer | B60P 3/228 141/95 |
| 2005/0067275 A1 * | 3/2005 | Kouchi | C02F 1/4674 204/269 |
| 2009/0277770 A1 * | 11/2009 | Malatesta | B01D 3/06 203/3 |
| 2011/0263909 A1 * | 10/2011 | Stankowiak | C09K 3/18 568/868 |
| 2013/0190539 A1 * | 7/2013 | Herron | C07C 29/86 568/919 |

* cited by examiner ial application of U.S. patent application
METHOD AND SYSTEM FOR RECYCLING SPENT ETHYLENE GLYCOL FROM RECOVERED AIRCRAFT DE-ICING SOLUTION This is a divisional application of U.S. patent application Ser. No. 14/999,007 filed on Mar. 17, 2016 and entitled Method and System for Recycling Spent Ethylene Glycol from Recycled Aircraft De-Icing Solutions.

TECHNICAL FIELD

The present invention relates to an improved method and a system for recycling spent ethylene or propylene glycol recovered from aircraft deicing solutions to produce virgin glycol having a concentration of at least 99.5% and up to 99.9%.

BACKGROUND ART

It is a requisite to de-ice the accumulation of frost, ice and snow or combinations thereof on the wings of aircrafts to restore the natural shape of the wings by removing any frost, ice or snow build-up that distorts its shape and to permit proper functioning of the ailerons Ice, frost or snow also adds to the weight of the aircraft, thereby impeding flight. The removal of frost, ice or snow is effected by spraying a de-icing glycol solution to cause the frost, ice or snow to melt away and protects the aircraft for sufficient time after de-icing against further precipitation. The concentration of glycol in the solution varies according to climatic conditions. Such solutions typically comprise glycol, water, and minor amounts of additives such as surfactants, and a corrosion inhibitor.

After spraying the de-icing solution on the aircraft, the solution becomes diluted with water from melted frost, ice and snow and becomes contaminated with pollutants present on the tarmac area where aircraft propagate to be de-iced. These areas are usually concrete areas polluted with sand, abraded rubber from aircraft tires, oil, combustion residue, fumes from the aircraft, deicing salts, grit, traces of fuel, solid debris such as grass and leaves, and chemicals found in concrete. In the past, such waste glycol solutions where harnessed in reservoirs or vacuum trucks for disposal and treatment at remote sites for disposal. Such a practice proved to be a burden on the environment and resulted in the loss of glycol which is an expensive product. Typically, the airport assumes the cost of this disposal and by recovering the spent glycol substantive savings is passed on to the airport facility.

Over the last decades, efforts have been made to recycle glycol residue from aircraft de-icing solutions and various recovery systems have been placed in operation using various methods such as aerobic digesters, cyclone separators, chemical cleaning techniques using absorption and ion exchangers, percolation towers, distillation and stripping columns or towers, etc. However, the operation of some of these have proven problematic and very costly and some have not achieved the desired sought after result of recovering glycol of sufficient purity comparable to purchased virgin glycol, for recycling for use in an aircraft deicing glycol solution. Some of the known techniques have claimed to recycle such glycol solutions to a purity of 99.5% but many have failed to produce this purity. Examples of known techniques can be found, for example, in the patent literature with reference to U.S. Pat. Nos. 5,904,321; 5,411,668; 7,713,319; 8,252,149; US Patent Application Publications 2011/0263909 and 2013/0190539, as well as Canadian Patents 2,116,827 and 2,223,922. Another publication on the topic of recycling glycol from airport tarmacs can be found in an article entitled "A Tour Of The Munich International Airport's Deicing Recycling Plant", such article being accessible on the web at http://www.aviationpros.com/article/10616425.

SUMMARY OF THE INVENTION

There is a need to provide an improved method and a system, which is substantially automatic, for recycling spent ethylene or propylene glycol recovered from aircraft deicing solutions to produce virgin glycol having a concentration of at least 99.5% and typically in the order of from between 99.6% to 99.9%.

It is a feature of the present invention to provide an improved method and system of recycling spent ethylene or propylene glycol recovered from aircraft deicing solutions and which meets the above mentioned need.

It is a further feature of the present invention to provide an improved method of recycling spent ethylene or propylene glycol from aircraft deicing solutions and wherein the method comprises the combination of an improved sequence of steps for treating of the reclaimed glycol solution and which steps are substantially automatically controlled to produce an aircraft de-icing glycol solution with a glycol concentration of at least 99.5% and typically in the order of from between 99.6% to 99.9%.

A further feature of the present invention is to provide an improved system for recycling spent ethylene or propylene glycol recovered from aircraft deicing solutions containing glycol, water and other impurities to produce a substantially virgin glycol having a concentration of at least 99.5% and typically in the order of from between 99.6% to 99.9%.

According to the above features, from a broad aspect, the present invention provides a method of recycling spent ethylene or propylene glycol recovered from aircraft de-icing solutions containing glycol, water and other substances to produce substantially virgin glycol. The method comprises, in combination, the steps of recovering spent glycol from the de-icing facilities of airports and storing the spent glycol in one or more storage tanks. Thereafter, the spent glycol having a predetermined low % concentration is removed to produce a working spent glycol and storing same in a storage means. The working spent glycol is filtered through at least two filtering stages to substantially remove all solids and other substances and stored in a holding tank. An evaporation step then removes water from a batch of filtered spent glycol by heating the batch to a temperature to evaporate water to bring the working spent glycol to a glycol concentration of about 50%. The glycol concentration solution is then stored in a buffer tank. The pH of the solution of glycol concentration of 50% is then adjusted to a desired value and then it is carbon filtered and fed to a holding tank which feeds a predetermined batch to an evaporator section of a distillation tower operating under vacuum where it is then heated to predetermined temperatures to evaporate the liquids in the glycol concentration of 50% in a stream of vapors. The temperature of the stream of vapor in a packing section of the distillation section of the tower is sensed to monitor the actual temperature of the stream of vapor and temperature signals representative thereof are sent to a computer controller. The stream of vapor at the top of the distillation tower is cooled as it exits from the packing section to condense into a liquid phase. The glycol concentration of the condensed liquid is monitored on a continuous basis to detect the glycol concentration of the condensed liquid and glycol concentration signals are sent to the computer controller which correlates these with the temperature signals to determine the appropriate time to operate valves to recover from the condensed liquid, in associated ones of reservoirs, water, water mixed with glycol below a concentration of 99.5%, and glycol solution of having a concentration of at least 99.5%. The water, water mixed with glycol below a concentration of 99.5%, and the glycol solution of at least 99.5% is automatically directed to associated reservoirs. The glycol of at least 99.5% is tested and blended and directed to certified holding tanks for use by aircraft de-icing vehicles.

According to a further broad aspect of the present invention there is provided a system for recycling spent ethylene or propylene glycol recovered from aircraft deicing solutions containing glycol, water and other substances to produce substantially virgin glycol. The system comprises, in combination, collection means for recovering spent glycol from the tarmac of an aircraft de-icing area. Storage means is provided for storing the recovered spent glycol. Means is further provided to remove spent glycol having a predetermined low % glycol concentration from the storage means. A working tank is also provided for maintaining a predetermined volume of the spent glycol having a glycol concentration above the predetermined low % glycol concentration. At least two filter stages is also provided to filter the spent glycol from the working tank to remove substantially all solid particles from the other substances and to feed it to a holding tank to feed an evaporator stage having one or more evaporators to evaporate water from the batch of spent glycol solution by boiling the batch at a temperature sufficient to evaporate water to produce a spent glycol having a glycol concentration of about 50% which is then transferred to a buffer tank. Means is provided to adjust the pH of the batch of glycol concentration from the buffer tank to a desired pH value and it is then carbon filtered and fed to a distillation tower holding tank to accumulate a predetermined volume of the spent glycol concentration above about 50%. A distillation tower is provided and operates under vacuum and has a lower evaporator section and an upper chimney section provided with steel packings to retain heat from a stream of vapors released from the lower evaporator section. Temperature sensors monitor the temperature of the chimney section along the packings to provide actual temperature signals to the computer controller representative of the actual temperature to the stream of vapors drawn through the packings and provides glycol concentration value signals to the computer controller. The lower evaporator section has a temperature controlled heater to evaporate the spent glycol in sequence to create the stream of vapors whose vapors are drawn through the chimney section and into a condensing coil downstream of the chimney section to produce condensed liquid which is fed through a cooling device. Measuring means is further provided to measure, on a continuous basis, the glycol concentration in the condensed liquid, and provide glycol concentration values to the computer controller to correlate with the temperature signals to determine the appropriate time to operate valves to separate, in associated reservoirs, water, water mixed with glycol having a glycol concentration of less than 99.5% purity, and substantially virgin glycol having a glycol concentration of at least 99.5% up to 99.9%. Means is then provided to certify and store the substantially virgin glycol in certified holding tanks ready for blending for use by aircraft de-icing vehicles.

BRIEF DESCRIPTION OF THE DRAWINGS

A preferred embodiment of the present invention will now be described with reference to the accompanying drawings in which.

DESCRIPTION OF THE PREFERRED EMBODIMENT

Figure 1A:
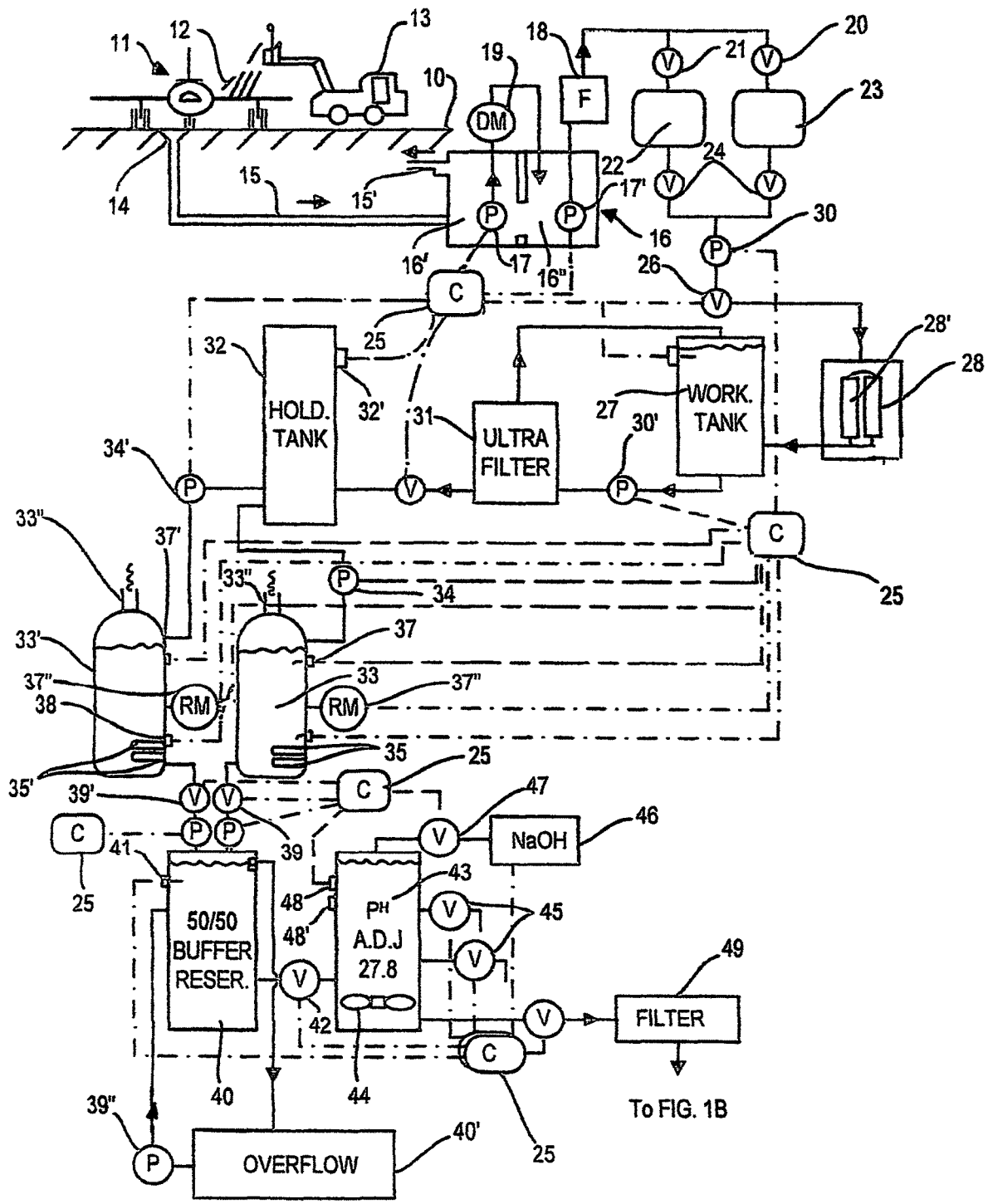
FIGS. 1A to 1C are schematic and partly block diagrams, illustrating the improved batch processing method and system of the present invention.

Referring to the drawings there will now be described a preferred embodiment of the improved method and system of the present invention for recycling spent ethylene or propylene glycol recovered from aircraft deicing solutions. As shown in FIG. 1A, the spent ethylene glycol herein of Type I or type IV is recovered from the tarmac 10 of an airport where aircrafts, such as the one schematically illustrated at 11, are sprayed with deicing solution 12 from deicing vehicles 13. The deicing solution is usually heated to a temperature of 60 to 80 degrees C. (centigrade). To recover spent glycol, the tarmac area is modified to be fitted with one or more storm drains 14 connected to underground conduits 15 to channel the spent glycol to a storage chamber 16 which is segmented. The spent glycol enters a first compartment 16' which also communicates with a larger chamber 16". The configuration of these chambers allows some sediments to precipitate at the bottom of chamber 16". A sample of spent glycol is continuously flowing through a densimeter 19 driven by pump 17 located in chamber 16' in order to assess the spent glycol concentration. If the concentration of the spent glycol is below 5%, the spent glycol is not suitable for recycling. Therefore, the computer controller 25 allows the level of spent glycol to gradually rise into chambers 16 until it reaches an overflow 15' to city sewage.

The computer controller 25 also operates a further pump 17' in the compartment 16" to pump solution of 5% or more concentration from the tank compartment 16" through a first filter 18 to remove sediments and feed the spent glycol of 5% or more concentration into holding tanks, herein only two tanks 22 and 23 being illustrated which are fitted with level detectors (not shown, but obvious to a person skilled in the art) to permit the computer controller to operate valves 21 and 20 to direct the spent glycol solution of 5% or more concentration to other holding tanks when a tank is full.

It is pointed out that the computer controller has various monitoring and control stations or different computers and such is identified throughout the drawings by the letter "C" inside a small square and reference numeral 25. It is also pointed out that throughout the drawings, the sizes of the squares, representing different units, tanks, filters, etc, are not representative of their size in proportion to one another.

From the storage tanks 22 and 23 the spent glycol solution of 5% or more concentration is treated substantially automatically by the computer controller 25, as follows by operating a valves 24 and a pump 30 spent glycol solution is subjected to a two stage filtering process. Firstly, the spent glycol is fed through a bag filter 28 and into a working tank 27 where a pump 30' circulates the filtered spent glycol concentration of 5% or more through an ultra fine filter 31, herein a ceramic filter, and back to the working tank 27 on a continuous basis. Ultra filtered spent glycol permeating through the ceramic filter by pressure is fed into holding tank 32 which has a level sensor 32' which when a predetermined volume of filtered spent glycol is reached, signals the computer controller to stop the pumps 30 and 30'. The bag filtering stage has two bag filters 28 and 28' to provide for longer uninterrupted operation by switching over to the other bag when one of the bags becomes clog with sediments. This permits longer operational time of the system. The ultra fine ceramic filter 31 has a pore size of 0.5 microns to remove very fine solid particles leaving substantially only liquids, often referred to as permeated liquid.

The filtered solution from holding tank 32 is then pumped, by pumps 34 and pump 34' into two evaporators 33 and 33' of like constructions. Each evaporator 33, 33' is provided with two electric resistive heating elements 35 and 35', respectively, which are operated by the computer controller 25 to ensure continuous operation of the evaporators in the event of failure of one of the resistive heating elements. Although not shown, these known evaporators 33 and 33' are each provided with a compressor (not shown) to extract heat from the vapors released in their flue 33" and re-use the heat from the vapors as a principal source to heat the water in the reservoirs. The resistive heating elements 35 and 35' are used to pre-heat the water at start-up, permitting the evaporation of water at lower temperature under vacuum conditions.

Level sensors 37 and 37' transmit level indicating signals to the computer controller 25 to operate the pumps 34 and 34' to provide sufficient spent solution in the evaporator whereby to switch one of the heating element on, the other being on stand-by and placed in service by a switch not shown, but obvious, in the event of failure of the other resistive heating element. Temperature sensing probes 38 provide actual temperature values to the computer controller of the batch solution in the evaporators 33 and 33'. The heating elements 35 and 35' are operated to control the temperature of the water to a boiling temperature of 100 degrees C. sufficient to evaporate water, but too low for ethylene or propylene glycol to evaporate. Refractometers 37" detect the density of the spent solution at an appropriate level and feeds representative signals to the computer controller 25 to operate valves 39 and 39' once the concentration of glycol attains 50% concentration. Valves 39 and 39' are operated to transfer batches of the spent glycol of 50% concentration to a buffer tank 40 on a continuous basis. The evaporators 33 and 33' operate on a continuous basis and as the volume of spent glycol solution in holding tank 32 drops to a predetermined level the pumps 30 and 30' are again actuated to filter more spent solution to feed ultra filtered solution to the holding tank 32. Any overflow from the buffer tank 40 is collected by gravity, as shown in FIG. 1A in reservoirs 40' for future use. In this embodiment there are several reservoirs 40' capable of holding 3 million liters of the solution of 50% glycol concentration. A pump 39''' supplies the solution back to the buffer tank 40 which was temporarily stored in the overflow reservoir 40' when needed to maintain the process continuously operational. Also, the buffer tank 40 is maintained inside a building to manage heat loss from the spent glycol of 50% concentration to save energy costs. In the preferred embodiment herein described, the buffer tank 40 holds 40,000 liters of the solution. Therefore, the overflow feature recovers any solution which exceeds the capacity of the tank and feeds.

After a desired volume, sensed by the signals from the level sensor 41, is present in the buffer tank 40, the computer controller 25 operates a transfer valve 42 and a pump, not shown but obvious, to transfer progressively some of the spent glycol solution over to a pH adjustment tank 43 provided with an agitator 44 for analysis as the volume of spent glycol solution in tank 43 is known as detected by level sensing probe 48 having informed the computer controller. The computer controller 25 also operates a transfer valve 47 and a pump, not shown but obvious, when the pH sensor 48', located in the tank 43, measures any low pH by amending the spent glycol solution with sodium hydroxide (NaOH) solution from reservoir 46. The pH is adjusted to a desired value of about 7.8 on the pH scale. Valves 45 are connected to the tank 43 at different levels. The adjusted pH spent glycol solution of 50% concentration is then fed through a carbon filter 49 to remove color and odors from the spent glycol solution before being stored into a distillation tower holding tank 50 where a predetermined quantity of the pre-treated spent glycol is maintained and controlled by level sensors.

Figure 1B:
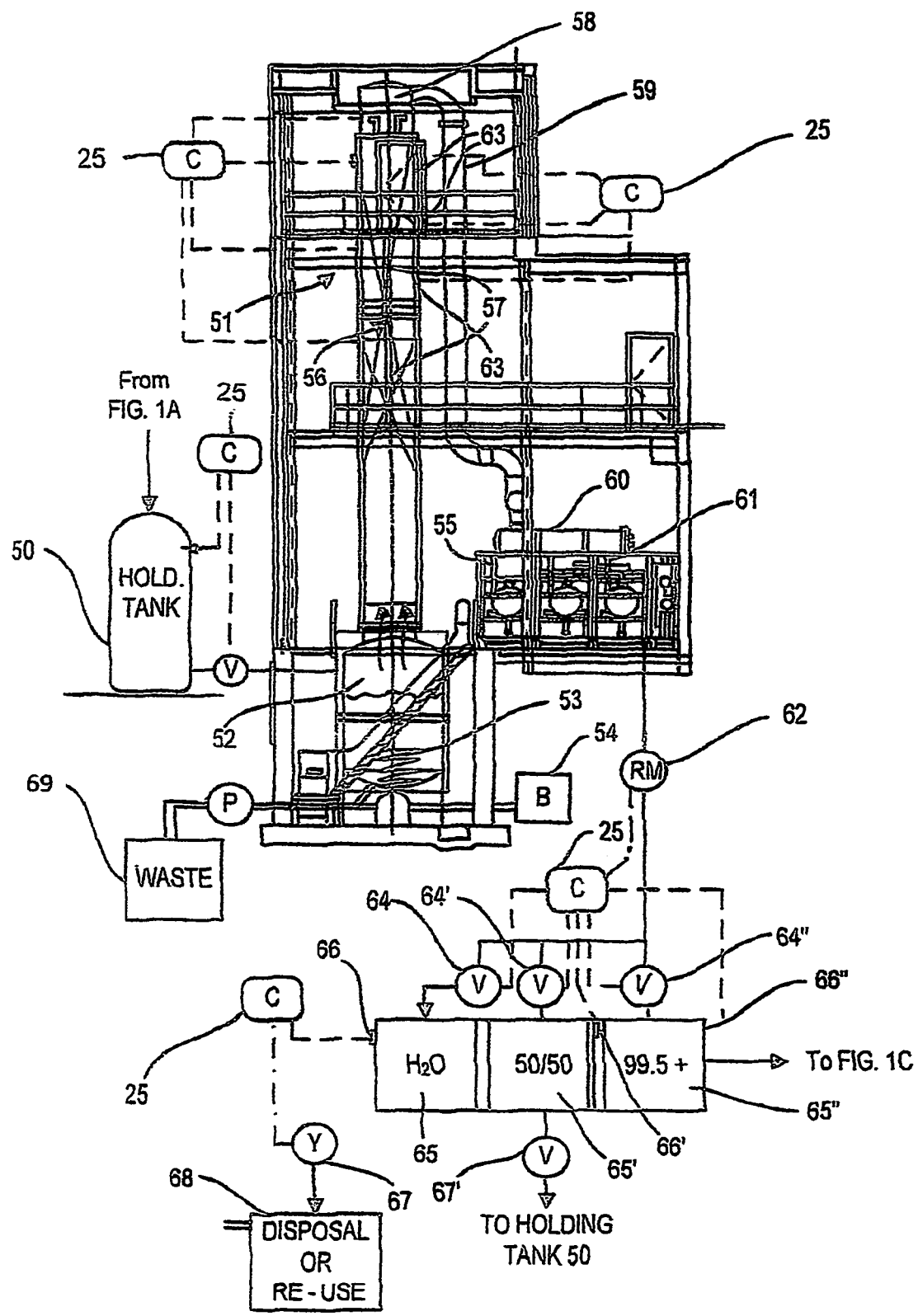

As shown in FIG. 1B, the process includes a distillation tower 51 which is essentially comprised of a bottom evaporator section 52 which includes a heating coil 53 in which is circulated, in a controlled manner, hot steam from a boiler 54 whereby to boil a predetermined batch of the spent glycol solution of 50% glycol concentration to evaporate substantially all of the liquid solution in the batch. Because the boiling temperature of water is far inferior to the boiling temperature of glycol, water will start evaporating as soon as the batch temperature reaches the boiling point of water. Accordingly, only water will evaporate at first, followed by water mixed with glycol, and lastly high concentration glycol. By controlling the flow rate of steam in the coil we can increase the temperature of the spent liquid in the evaporators section to evaporate the liquids in stages. Once all the liquids have evaporated, the sensed temperature in the packings will drop providing an indication that the entire batch is evaporated.

A vacuum pump 55 connects to the distillation tower 51 at an appropriate downstream location outside the tower to place the tower under vacuum. The distillation tower has a chimney section 56 above the evaporator section 52 and in which there is provided metal packings 57, herein stainless steel corrugated perforated sheets which accumulate heat from the hot stream of vapors released from the boiling liquid in the evaporator section. The temperature of the vapor passing through the packings is monitored by temperature sensors 63 feeding temperature signals to the computer controller 25 to provide an indication of the temperature of the stream of steam giving an indication of its content in relation to its temperature. These temperature signals also indicate the start and the end of the evaporation cycle. The temperature sensors may be in the form of thermistors retained biased and spaced apart vertically against the wall of the chimney section. The distillation tower is also thermally insulated by a shroud spaced about the inner casing with an appropriate insulation material disposed there between, much like the insulated tank of a water heater. The boiler is heated with natural gas and circulates sufficiently high temperature steam through the heating coil 53 whereby the boiling water temperature rises substantially quickly to the boiling point of glycol which is about 197 degrees C. which is far greater than the boiling point of water. The density of glycol is about 1.1132 g/cubic centimeter. It is pointed out that the vacuum conditions in the distillation tower decreases slightly the boiling points of each liquid to be evaporated, namely water and glycol, and this also provides an energy cost saving.

At the top of the chimney section 56 there is mounted a condenser 58 which condenses the stream of vapor as it exits the distillation tower 51 to turn the vapor into its liquid phase. The condensation is outside the chimney whereby the condensate does not fall back into the chimney section. As mentioned, because the water evaporates earlier than the glycol, at the beginning of the evaporation process, mostly water is condensed and the condensate with some vapor is channeled by a long conduit 59 where further condensation takes place and into a further cooler 60 where any residual vapor is condensed. Nothing is released into the atmosphere to prevent the loss of glycol. Secured to an outlet pipe 61 of the cooler 60 is a refractometer 62 which measure the glycol concentration of glycol which may be contained in the condensed liquid and feeds its readings to the computer controller 25, which in correlation with temperature signals received from the chimney section, determines the proper time to operate valves 64, 64' and 64" associated with a respective one of three reservoirs or tanks 65, 65' and 65".

When only water is detected, valve 64 is open and the other two valves 64' and 64" are closed thereby to channel the water into reservoir 65 for disposal or re-use. When computer controller 25 determines that the condensate liquid contains glycol mixed with water, the computer controller 25 closes valves 64 and 64" and opens valve 64' to channel the mixture into reservoir 65' until the computer controller determines from its correlated signals that the glycol concentration about 99.5%. The computer controller then closes the valves 64 and 64' and opens valve 64" to channel the remaining glycol which is classified as virgin glycol into reservoir 65". Preferably, the condensed liquid is switched over to reservoir 65" when the computer controller 25 receives condensate signals indicating 99.6% to 99.9% glycol concentration in the solution from refractometer 62 which is classified as virgin glycol. Level sensors 66, 66' and 66" provide signals to the computer controller indicating the volume of liquid in its associated reservoirs whereby to evacuate its contents to appropriate locations. Valve 67 dispenses the recovered water for appropriate storage in tank 68 for disposal or re-use. Valve 67' permits its content to be transferred back into the holding tank 50 to be re-introduced into the distillation tower. Finally, residual material consisting of high boiling point compounds collect in the sump lower section of the evaporator section and is pumped into a waste tank 69 at the end of the evaporation cycle and another batch is introduced for evaporation and separation.

Figure 1C:
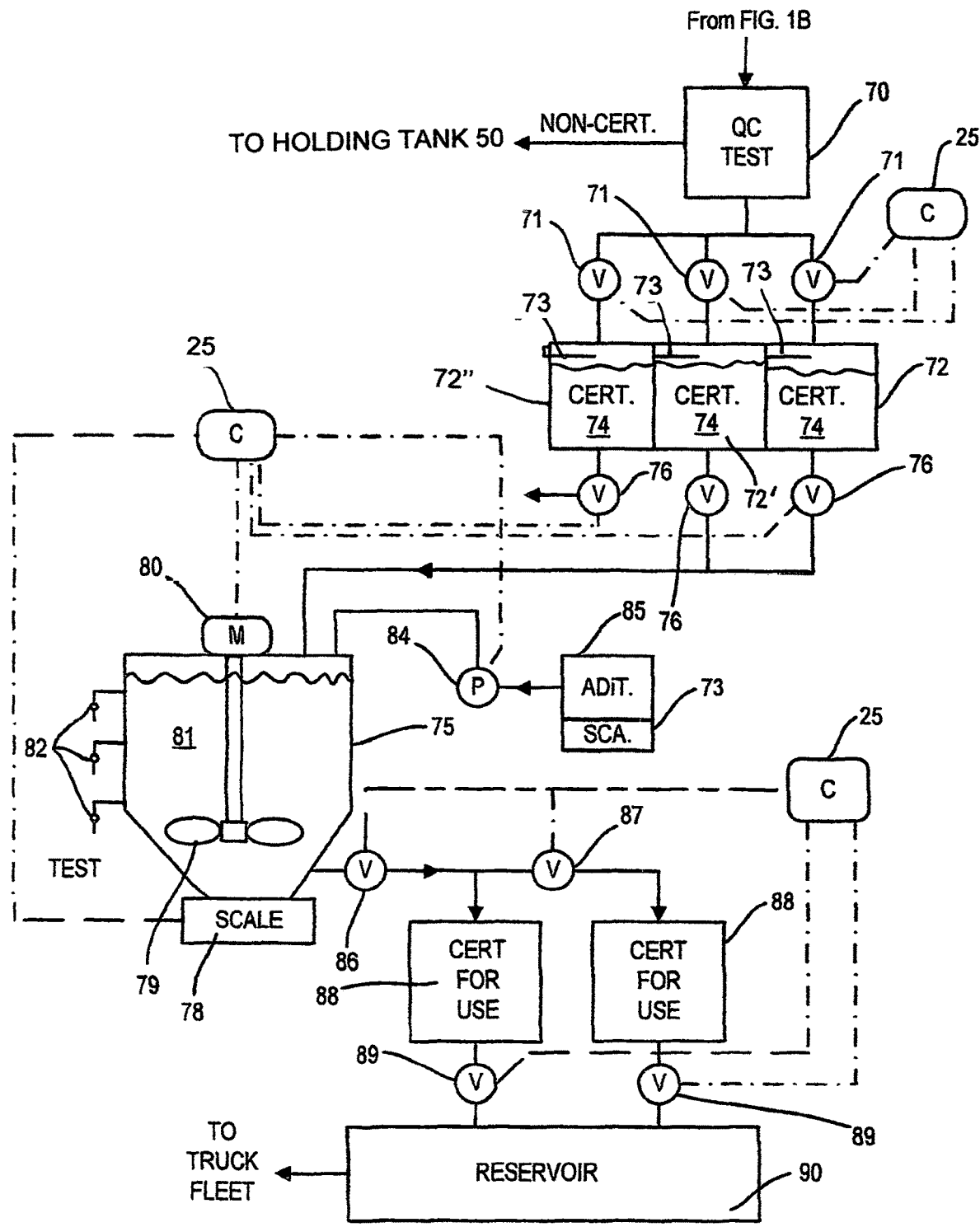

Referring now to FIG. 1C, it can be seen that the glycol solution batch from reservoir 65" is now subjected to a further quality control testing in a further reservoir 70 to certify its glycol concentration by measuring the Fisher methodology, the Brix and testing of the pH. Sampling valves (not shown) are provided at various levels of the reservoir 70 for the extraction of samples for lab analysis. After certification, the computer controller 25 operates valves 71 to transfer the certified glycol into certified reservoirs 72. The contents of the reservoir 72 is monitored by level sensors 73 feeding information signals to the computer controller 25 whereby the content can be safely transferred and to indicate that the valves 71 need to be operated to switch the transfer of solutions to other reservoirs 72, 72' and 72". With the batch process of the present invention the concentration of the recycled glycol in the solution can be brought up to 99.9% whereby it achieves a very high level of purity which is very important to provide a final solution of near perfect concentration, the requisite for virgin glycol of the highest purity to assure for a perfect blended de-icing solution for re-use.

At this point in the process, the certified glycol solution 74 in one or several reservoirs 72 need to receive further final additives and this is effected in a blending tank 75. The solution 74 is transferred into the blending tank by the computer controller 25 operating selected ones of transfer valves 76 until the blending tank is filled with a predetermined weight as sensed by a scale 78 mounted under the blending tank 75. Once the scale 78 indicates that the blending tank has received its volume of glycol solution 74, the computer controller 25 shuts off the valve(s) 76. At this point ADF blending is done by the addition of additives 85, also sensed by a scale 73, which are introduced into the solution content 81 by operating pump 84 to bring the fluid solution to a desired concentration, for example 88%. An agitator 79 is operated by switching on its motor 80 to mix the glycol solution content 81. Sampling valves 82 permit sampling the content 81 after the agitating cycle to effect tests, testing the pH, and the refracting index to assure that the content 81 can be certified as a type I de-icing glycol. Valves 86 and 87, controlled by the computer controller 25 direct the final adjusted certified solution to additional reservoirs 88 equipped with valves 89 for dispensation to farm tank 90 at a location accessible to aircraft deicing vehicles. These vehicles effect on-line blending of the deicing glycol solution by adding water which may have been recovered in the process, depending on the outside temperature, to adjust the glycol concentration.

It is within the ambit of the present invention to cover any obvious modifications of the preferred embodiment described, provided such modifications fall within the scope of the appended claims.

The invention claimed is:
1. A method of treating spent ethylene or propylene glycol recovered from aircraft de-icing solutions containing glycol, water, solids and other substances to produce substantially virgin glycol, said method comprising, in combination, the steps of:
  i) recovering in a collection reservoir, having a segmented storage compartments, spent glycol from a tarmac of aircraft de-icing area to permit sampling by pumping said spent glycol solution through a densimeter to determine the glycol concentration in said spent glycol,
  ii) removing spent glycol having a predetermined low % concentration from the collection reservoir to produce a working spent glycol and pumping said working spent glycol in one or more storage a-tanks,
  iii) filtering said working spent glycol from said one or more storage tanks through at least two filtering stages to substantially remove all remaining solids and substances followed by an evaporation step wherein said working spent glycol is heated to a temperature sufficient to evaporate only water to bring said working spent glycol to a glycol concentration of about 50% for storage in a buffer tank,
  iv) transferring said glycol having a concentration of about 50% purity to said buffer tank,
  v) transferring a predetermined volume of said glycol having a concentration of about 50% purity from said buffer tank to a pH adjusting mixing and sampling tank,
  vi) sampling and adjusting the pH of said glycol concentration of about 50% purity in said pH adjusting mixing and sampling tank by agitation and the introduction of an additive to adjust the pH to a desired value and then carbon filtering said glycol concentration of about 50% purity and feeding same to a distillation tower holding tank,
  vii) feeding a predetermined volume of said carbon filtered glycol concentration of about 50% purity from said distillation tower holding tank to an evaporator section of a distillation tower operating under vacuum,
  viii) heating in an evaporator section of said distillation tower said batch at a predetermined temperature to evaporate said glycol concentration of about 50% purity in a continuous stream of vapors, ix) sensing the temperature of said stream of vapors in a hot packing section of a chimney section spaced above said evaporator section to monitor the actual temperature of said stream of vapors and feeding temperature signals representative thereof to a computer controller, x) condensing said stream of vapors after said stream of vapors exits said chimney section to condense said stream of vapors and cooling it into a condensed liquid, xi) monitoring on a continuous basis by said computer controller (a) said temperature signals to correlate same with the evaporation temperature of water and glycol, and (b) glycol concentration signals form a refractometer located in a conduit through which flows said condensed liquid, to recover from said condensed liquid, in separate reservoirs, and by the operation of valves, water, water mixed with glycol below a concentration of 99.5% purity, and substantially virgin glycol having a concentration of at least 99.5%, xii) directing said substantially virgin glycol from its associated reservoir for further testing and certification of the purity thereof and storing same in certified holding tanks for use by aircraft de-icing vehicles, and directing said water from said separate reservoirs to a storage tank for disposal or re-use and directing said water mixed with glycol having a glycol concentration less than 99.5% purity to a holding tank feeding said evaporator, and xiii) quality testing said substantially virgin glycol having a concentration of at least 99.5% purity to certify and store same in certified holding tanks for use by aircraft de-icing vehicles.

2. The method of claim 1 wherein said substantially virgin glycol of step (xi) has a concentration in the range of from about 99.6% to 99.9% purity and further wherein after step (xii) of certification of the purity thereof and storing same in certified holding tanks in step (xii), there is provided the further step of blending said certified glycol solution of from about 99.6% to 99.9% purity into a blending tank where additives are blended with said certified substantially virgin glycol.

3. The method of claim 1 wherein in step (xi) said separated water mixed with glycol below a concentration of 99.5% purity and collected in associated reservoirs is fed back to a holding tank of said distillation tower to be re-introduced into said distillation tower for further evaporation, said step (vii) further comprising feeding said predetermined volume of carbon filtered glycol concentration in said holding tank of said distillation tower.

4. The method of claim 1 wherein in said step (ii) said spent glycol having a predetermined low % purity has a concentration of below 5% purity, is caused to rise in a compartment of said segmented storage means to an overflow conduit for disposal to sewage.

5. The method of claim 1 wherein in said filtering step (iii) one of said at least two filtering stages comprises a 5 micron bag filter which feeds filtered glycol solution to a working tank and wherein said filtered glycol solution from said working tank is pumped in a continuous loop and through a 0.5 micron ceramic filter, said working spent glycol being filtered in said continuous loop to achieve a desired ultra-filtered spent glycol free of substances of particle size above 0.5 microns, and feeding said ultra-filtered spent glycol to a further holding tank which feeds said filtered spent glycol to one or more evaporators.

6. The method of claim 5 wherein said further holding tank is provided with level sensing means to provide level signals to said computer controller which controls the operation of said continuous filtering loop, said evaporators being operated on a continuous basis and having level sensing means to permit said computer controller to dispense filtered spent glycol solution thereto to maintain a predetermined volume of said filtered spent glycol solution in said one or more evaporators.

7. The method of claim 6 wherein said one or more evaporators are each provided with two electric resistive heating elements connected for independent operation through switch means operated by said computer controller to ensure continuous operation of said evaporator in the event of failure of one of said resistive heating elements, a densimeter associated with each said one or more evaporators to detect the glycol concentration in a predetermined area of said evaporators to feed glycol concentration signal values to said computer controller which operate valves connected to each said evaporators to discharge spent glycol solution having a concentration of 50% purity from a bottom region of said one or more evaporators into said buffer tank and to shut off said valves when said concentration signal values fall below a glycol concentration of 50% purity.

8. The method of claim 1 wherein said glycol concentration of about 50% purity stored in said buffer tank is subjected to a pre-treatment as defined by step (vi) by the addition of NaOH (sodium hydroxide) in an agitator tank as desired to adjust the pH to said desired value, said desired value being about 7.8 on the pH scale, and further wherein said carbon filtering of step (vii) is to remove color and odors from said glycol concentration before feeding same to a holding tank of said distillation tower where a control level of said pre-treated glycol concentration of 50% purity is maintained for batch feeding an evaporator section of said distillation tower.

9. The method of claim 1 wherein said evaporator section of said distillation tower has a heating coil in which is circulated hot steam from a boiler to evaporate in said stream of vapors said predetermined batch of glycol concentration of 50% purity, a vacuum pump connected to said distillation tower downstream of said evaporator section, said hot packing section having a plurality of stainless steel packings which are heated along said chimney section by said stream of vapors, and wherein after said step (x) and before said step (xi) there is provided the further step of feeding said condensed liquid into a cooler device to achieve complete condensation.

10. The method of claim 2 wherein said step (xiii) comprises feeding said substantially virgin glycol having a concentration of at least 99.5% purity for said certified holding tanks to a blending tank which is provided with level tap valves to permit testing of the pH, the clarity, the Brix and refracting index of said substantially virgin glycol at different levels of said blending tank, and wherein the volume of said substantially virgin glycol in said blending tank is determined by a scale disposed under said blending tank, and pumping means to pump said substantially virgin glycol from said blending tank to further certified holding tanks for use by said de-icing vehicles.

* * * * *